(12) United States Patent
Uchikubo

(10) Patent No.: US 7,386,730 B2
(45) Date of Patent: Jun. 10, 2008

(54) REMOTE MEDICAL SUPPORTING SYSTEM

(75) Inventor: Akinobu Uchikubo, Iruma (JP)

(73) Assignee: Olympus Corporation, Tokyo (JP)

( * ) Notice: Subject to any disclaimer, the term of this patent is extended or adjusted under 35 U.S.C. 154(b) by 673 days.

(21) Appl. No.: 10/234,875

(22) Filed: Sep. 4, 2002

(65) Prior Publication Data

US 2003/0046562 A1    Mar. 6, 2003

(30) Foreign Application Priority Data

Sep. 5, 2001    (JP) ............................. 2001-269302

(51) Int. Cl.
| H04K 1/00 | (2006.01) |
| A61B 1/00 | (2006.01) |
| A61B 17/00 | (2006.01) |
| G06F 7/00 | (2006.01) |

(52) U.S. Cl. .................. 713/182; 600/118; 707/104.1; 606/1

(58) Field of Classification Search ................ 713/182; 600/118; 707/104.1; 606/1
See application file for complete search history.

(56) References Cited

U.S. PATENT DOCUMENTS

| 5,740,801 | A | * | 4/1998 | Branson ...................... 600/407 |
| 5,868,666 | A | * | 2/1999 | Okada et al. ................ 600/118 |
| 5,902,230 | A | * | 5/1999 | Takahashi et al. .......... 600/109 |
| 6,106,457 | A | * | 8/2000 | Perkins et al. .............. 600/175 |
| 6,272,470 | B1 | * | 8/2001 | Teshima ........................ 705/3 |
| 6,393,431 | B1 | * | 5/2002 | Salvati et al. ............ 707/104.1 |
| 6,424,996 | B1 | * | 7/2002 | Killcommons et al. ..... 709/206 |
| 6,491,701 | B2 | * | 12/2002 | Tierney et al. .............. 606/130 |
| 6,611,846 | B1 | * | 8/2003 | Stoodley ................... 707/104.1 |
| 6,622,050 | B2 | * | 9/2003 | Thompson .................... 607/60 |
| 6,725,200 | B1 | * | 4/2004 | Rost .............................. 705/3 |
| 6,819,785 | B1 | * | 11/2004 | Vining et al. ................ 382/128 |
| 6,889,324 | B1 | * | 5/2005 | Kanai et al. ................. 713/176 |
| 6,948,069 | B1 | * | 9/2005 | Teppler ....................... 713/178 |
| 7,028,182 | B1 | * | 4/2006 | Killcommons .............. 713/161 |
| 2001/0027331 | A1 | * | 10/2001 | Thompson .................... 607/60 |
| 2002/0055917 | A1 | * | 5/2002 | Muraca ......................... 707/1 |
| 2003/0060808 | A1 | * | 3/2003 | Wilk ............................. 606/1 |

FOREIGN PATENT DOCUMENTS

| JP | 2000-245738 | 9/2000 | ..................... 606/1 |
| JP | 2000-270318 | 9/2000 | ..................... 606/1 |

\* cited by examiner

*Primary Examiner*—Emmanuel L Moise
*Assistant Examiner*—Techane J. Gergiso
(74) *Attorney, Agent, or Firm*—Scully, Scott, Murphy & Presser, P.C.

(57) ABSTRACT

When a surgery and a remote control room in a remote location are connected through a communication circuit to perform an endoscope operation, image information is not encrypted and is sent as it is. Patient data including identification information, a name and so on relating to a patient is encrypted in an encrypting portion and then is sent. In the remote control room side receiving the patient data through the communication circuit, the patient data is decrypted by a decrypting portion when it is determined, based on the header portion, that the received data includes the patient data. Thus, the patient data is restructured and a structure, which can be displayed in a display device, including the image information can be obtained. As a result, the privacy of the patient data can be reserved, and the fast transmission can be achieved at low costs.

24 Claims, 7 Drawing Sheets

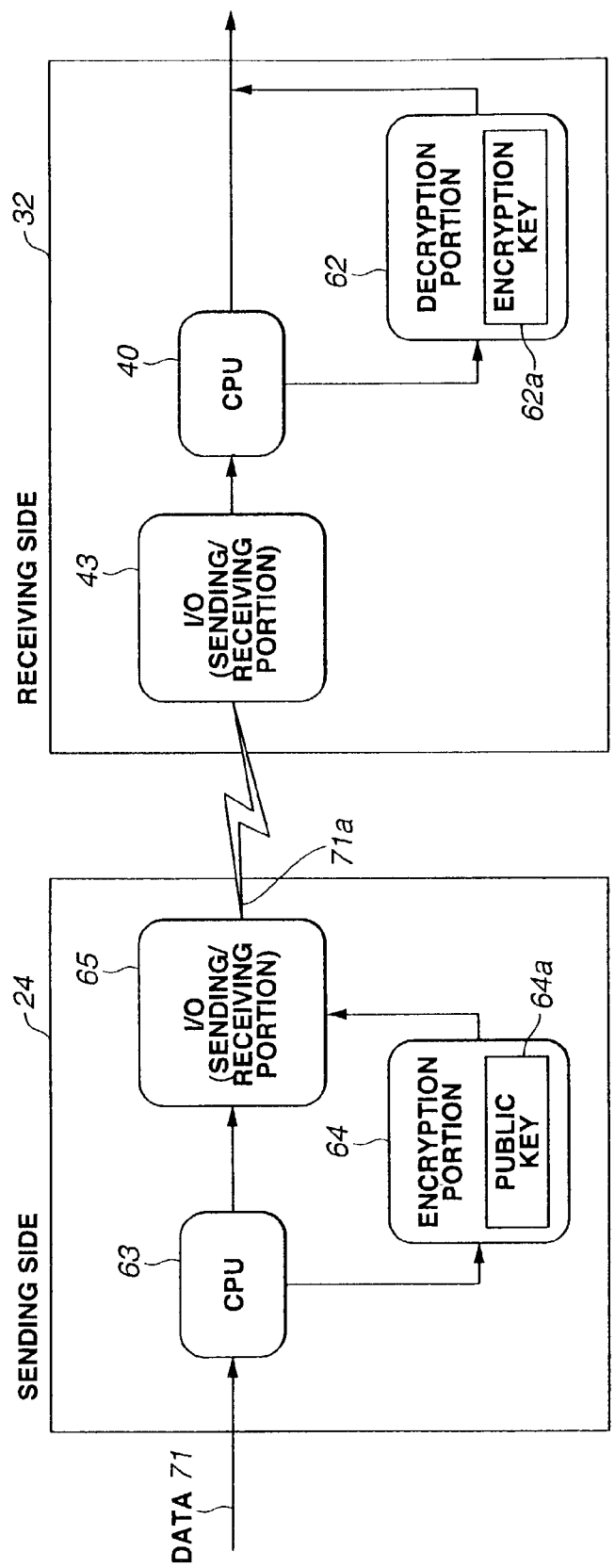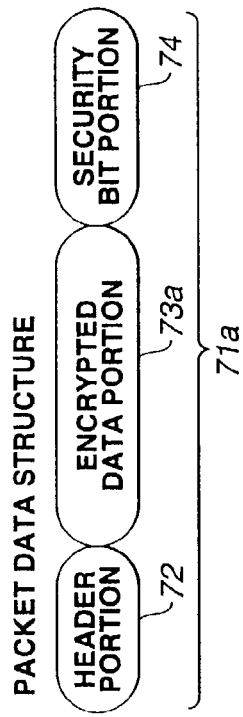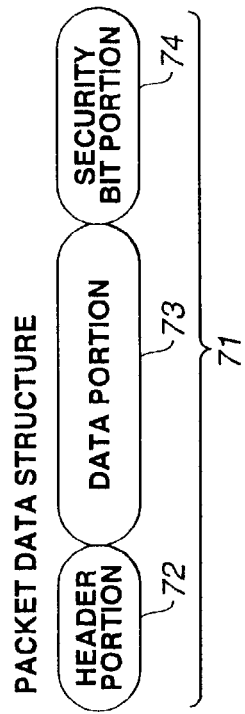

REMOTE MEDICAL SUPPORTING SYSTEM

This application claims benefit of Japanese Application No. 2001-269302 filed on Sep. 5, 2001 the contents of which are incorporated by this reference.

BACKGROUND OF THE INVENTION

1. Field of the Invention

The present invention relates to a remote medical supporting system, which can transmit medical images and so on remotely.

In general, an operation is performed on a patient by an operator in a surgery. However, if the operator in the surgery is required to perform an operation for which he/she does not have much experience in past, a supporting system may be considered. The supporting system provides the operator with a connection to a supporting operator in a remote place (remote supporting operator) who is familiar with the operation over a network. Then, during the operation, the remote supporting operator can give instructions and so on regarding a part to be resected. Then, the proper operation can be performed on the patient in the surgery.

2. Description of the Related Art

One of the medical information transmission systems of the related art, which supports an operation remotely as such is Japanese Unexamined Patent Application Publication No. 2000-270318.

According to the related art, not only endoscope images but also an operating condition of a surgery tool and personal information (identification information) of the patient are transmitted to the remote operation supporter. Yet, the security for the transmission is not disclosed. However, in order to encrypt a large amount of moving images in real-time, the cost is increased and the real time characteristic is prevented.

SUMMARY OF THE INVENTION

Accordingly, it is an object of the present invention to provide a remote medical supporting system, which can allow the fast transmission to a remote place by achieving the security of identification information of a patient and, at the same time, by minimizing the deterioration in the transmission speed and an increase in costs.

It is another object of the present invention to provide a remote medical supporting system having a simple configuration, which is widely applicable.

According to an aspect of the present invention, there is provided an operation supporting system, which is used for an operation, including an imaging device for imaging a subject part of a patient and for outputting an image signal, an information input device for inputting identification information of the patient, a first controller for encrypting the identification information input from the information input device, a sending device for sending an encrypted information encrypted by the first controller and the image signal output from the imaging device, a receiving device for receiving the encrypted information and the image signal sent from the sending device, a second controller for decrypting the encrypted information received by the receiving device, and a display device for displaying the identification information decrypted by the second controller and the image signal from the receiving device. Thus, a large amount of image signals are not encrypted and are sent. Only identification information of the patient is encrypted and is sent. Therefore, the security of the identification information of the patient can be reserved while the fast transmission to a remote location can be performed by minimizing the deterioration in transmission speed and an increase in costs.

BRIEF DESCRIPTION OF THE DRAWINGS

FIGS. 1 to 5 relate to a first embodiment of the present invention; FIG. 1 is a block diagram showing the configuration of a remote medical supporting system according to the first embodiment;

FIG. 2 is a block diagram showing the configuration of a controller in a remote supporting device portion side in FIG. 1;

FIG. 3 is a diagram showing an example of a screen displayed by a display device in FIG. 1;

FIG. 4A is a diagram showing the configuration of encryption and decryption between a sending side and a receiving side;

FIG. 4B is a diagram showing a packet structure of data to be sent;

FIG. 4C is a diagram showing that a data portion is encrypted when data in FIG. 4B is patient data;

FIG. 5 is a diagram showing the construction of encryption and decryption in a variation example;

FIG. 6 is a block diagram showing a configuration of a remote medical supporting system according to the second embodiment;

FIG. 7 is a diagram showing that an identification code is given in a header portion of encrypted data; and FIG. 8 is a diagram showing that encrypted patient data or the like is displayed in a display form, which can be easily distinguished from other character information.

DESCRIPTION OF THE PREFERRED EMBODIMENTS

A first embodiment of the present invention will be described with reference to FIGS. 1 to 5.

Figure 1:
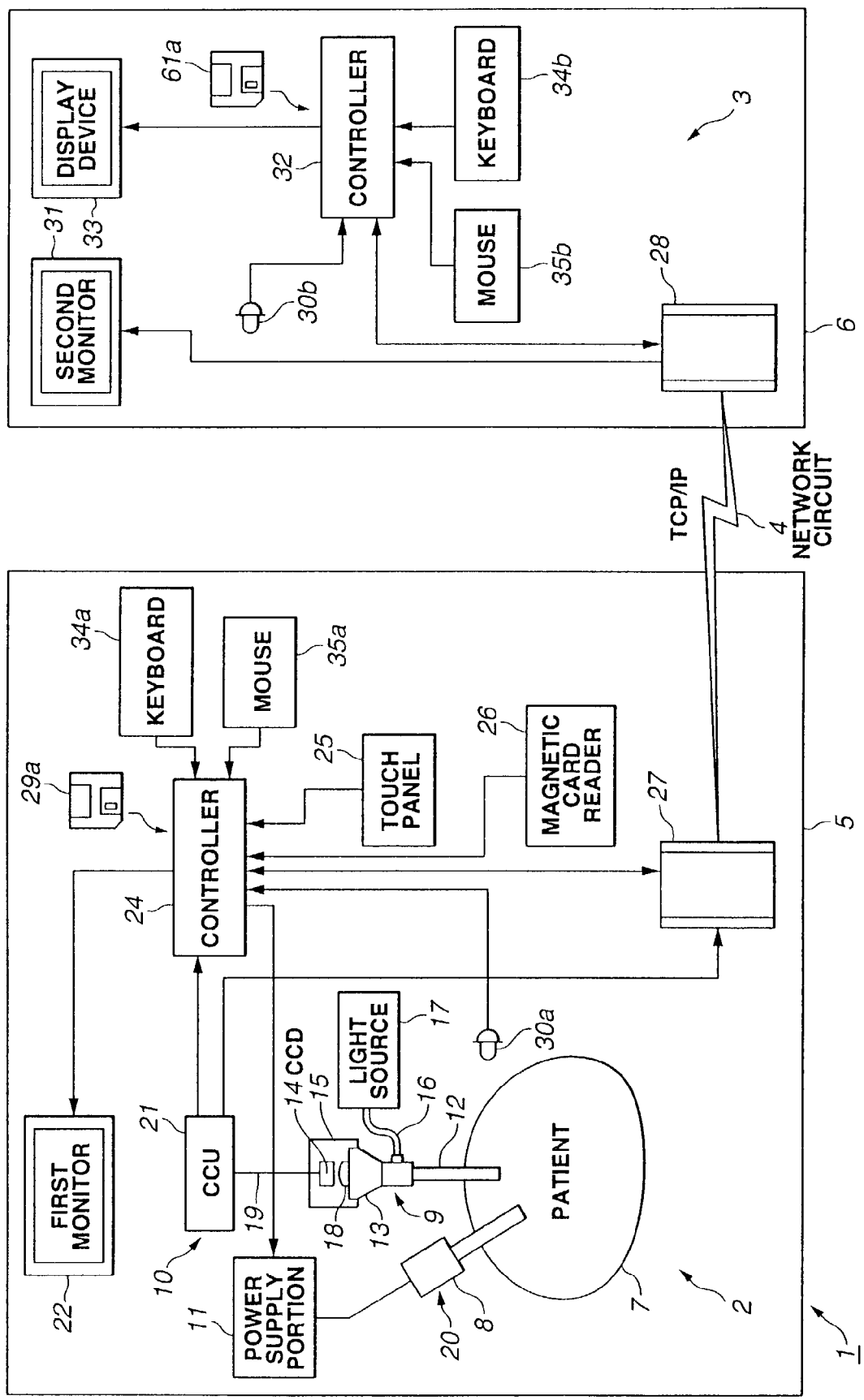

As shown in FIG. 1, a remote medical supporting system 1 according to the first embodiment of the present invention includes an endoscope operating device portion (simply called operating device portion hereinafter) 2, which performs an operation under, for example, the endoscope operation, and a remote supporting device portion 3 located in a remote place with respect to the operating device portion 2. The remote supporting device portion 3 and the operation device portion 2 are connected through a network circuit 4. The operating device potion 2 and the remote supporting device 3 are located in a surgery 5 and a remote control room (remote supporting device room) 6, respectively.

The operating device portion 2 located in the surgery 5 has an endoscope imaging device 10, which is used to observe inside of a body cavity of a patient 7 and an operating device (surgery tool) 20, which is used to perform an operation for treating the patient 7 under the observation by using the endoscope imaging device 10.

More specifically, a surgery tool body 8, which is used to perform a treatment operation and an optical endoscope 9, which is used to observe an operation condition by using the surgery tool body 8 are inserted to an abdominal part, for example, of the patient 7.

The surgery body 8 is a device, which is used to perform treatment such as resection by using an electric knife, for example, and coagulation. The surgery tool body 8 is connected, through a cord, for example, to a power supply (or power supply and control portion) 11 having functions of supplying drive power to the surgery tool body 8 and of variably setting an output value in accordance with the resection or coagulation mode. The surgery tool 20 includes the surgery tool body 8 and the power supply portion (power supply and control portion for some treatment tools).

The endoscope 9 is a rigid endoscope having a rigid inserting portion 12, for example. A television camera 15 self-containing a charge coupled device (abbreviated as CCD 14), for example, which is an imaging element, is attached to an objective portion 13 provided in the back end side of the inserting portion 12. Thus, a unit adjusted to image endoscope images is formed.

A light guide cable 16 of the endoscope 9 is connected to a light source device 17. Illuminating light from a lamp, not shown, within the light source device 17 is transmitted through a light guide within the light guide cable 16 and a light guide within the endoscope 9. Then, the illuminating light transmitted from a light guide pointed end surface, which is fixed to an illuminating window of a pointed end side of the inserting portion 12 is emitted to illuminate an object side such as an organ within the body cavity.

An objective lens, not shown, is mounted to an objective window adjacent to the illuminating window and focuses an optical image of the object. The optical image is transmitted to the back side by using a relay lens system, for example, which is an optical image transmitter located within the inserting portion 12. Thus, the magnified observation can be achieved through the objective lens, not shown, of the objective portion 13.

The optical image is focused, which is transmitted to the CCD 14 through an imaging lens 18 of the television camera 15 attached to the objective portion 13 removably. The CCD 14 is connected to a camera control unit (abbreviated as CCU hereinafter) 21 through a signal cable 19. An endoscope imaging device 20 performs signal processing on signals, which is photoelectrically converted in the CCD 14, and generates standard video signals.

The video signals are output from the CCU 21 to a first monitor 22. Then, endoscope images such as a body cavity internal organ and the pointed end side of the surgery tool body 8 for performing an operation thereon imaged by the CCD 14, are displayed.

The video signals from the CCU 21 are output to a first controller 24. Then, the endoscope images of, for example, the body cavity internal organ and the pointed end side of the surgery tool body 8 for performing an operation thereon, which are imaged by the CCD 14 are displayed in the first monitor 22 through the first controller 24. The CCU 21 and the power supply portion 11 are connected to the (first) controller 24, which is adjusted to control them, for example. The controller 24 is connected to, for example, a touch panel 25, which is used to input control instructions, and is connected to, for example, a magnetic card reader 26, which is used to input patient data and so on.

Thus, the color control such as changing a color and the output control for the surgery tool body 8 can be performed by manipulating the touch panel 25, for example, for the CCU 21 through the controller 24. For example, when the surgery tool body 8 is an electric knife, the setting of the output level for resection, coagulation or the like by using the electric knife can be controlled. In addition, when the treatment tool 20 is a pneumoperitoneum apparatus, the variable setting of values for set pressure and so on can be controlled.

Furthermore, patient data recorded in a magnetic card can be read by the magnetic card reader 26. Then, the patient data can be input to the controller 24. Thus, the patient data can be superimposed and displayed on an endoscope image through the controller 24.

The CCU 21 and the controller 24 provided in the surgery 5 are connected to a (first) signal transmitting device 27. The output from the CCU 21 is displayed on the first monitor 22.

Analog video signals of an endoscope image are converted to signals,-which can be transmitted to the network circuit 4 such as an ATM circuit by the signal transmitting device 27. Thus, the converted signals can be transmitted to a (second) signal transmitting device 28 in the remote control room 6 side through the circuit 4.

Signals sent from the signal transmitting device 28 in the remote control room 6 side to the signal transmitting device 27 through the network circuit 4 are converted to video signals. The video signals are output to the first monitor 22 through the controller 24 connected to the signal transmitting device 27. Thus, image information and the like from the signal transmitting device 28 side can be overlay-displayed on the first monitor 22.

Control signals or character information such as patient data from the controller 24 are converted to signals, which can be transmitted through the circuit 4 by the signal transmitting device 27. Thus, the converted signals can be transmitted to the signal transmitting device 28 in the remote control room 6 side through the circuit 4.

In this case, as described later with reference to FIG. 4A and so on, when patient data including identification information, such as a record number, is sent, the patient data is identified from the header portion of a data packet including the patient data, and the part is encrypted and sent. Then, in the receiving side, the encrypted patient data part is decrypted so as to restructure the patient data. Thus, security can be maintained such that the privacy for the patient information (that is, personal information) can be protected.

A removable storage device such as a photomagnetic disk device is provided to the controller 24. A removable medium 29a such as a photomagnetic disk is mounted to the removable storage disk removably. Thus, image data, patient data and so on can be recorded.

A microphone 30a is connected to the controller 24. An operator in the surgery 5 can voice-input comments and so on from the microphone 30a. The voice data can be sent from the controller 24 to the remote control room 6 side through the signal transmitting device 27 and so on.

A microphone 30b is connected to a controller 32 in the remote control room 6 side. Support information from the remote supporting operator side can be sent as voice information from the microphone 30b to the surgery 5 side.

A keyboard 34a and a mouse 35a are connected to the controller 24 in FIG. 1. Cursor position information and so on can be sent from the mouse 35a to the signal transmitting device 28 in the remote operator side through the controller 24.

Figure 2:
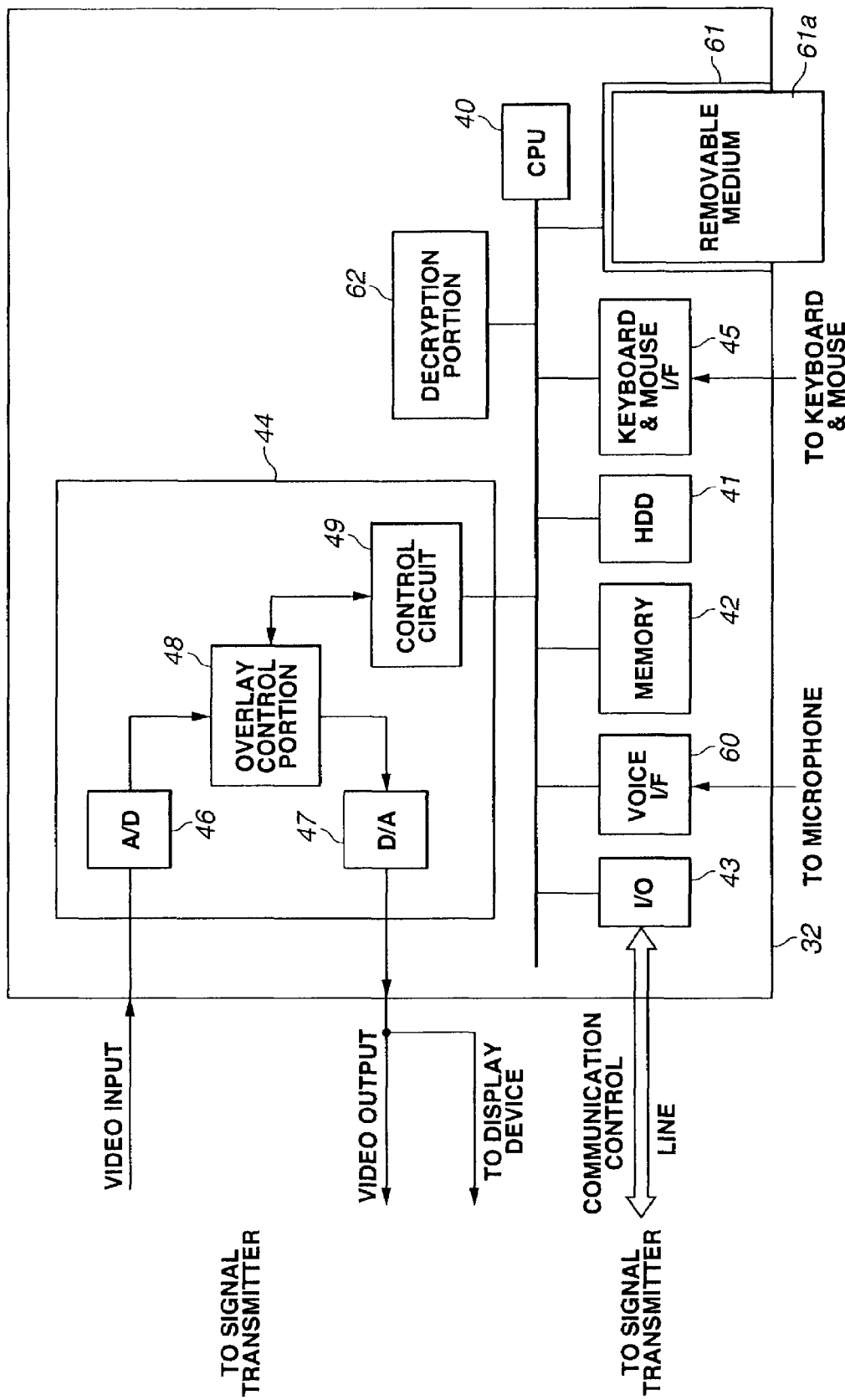

FIG. 2 shows the construction of the controller 32. The controller 32 includes a central processing unit (abbreviated as CPU hereinafter) 40, which performs control operations, a hard disk (abbreviated as HDD) 41, which stores operational programs for the CPU 40, images and so on, a memory 42, which is used as an image temporary storage area, a work area and so on, an I/O 43, a video capture control portion 44, which performs capture operations and superimpose operations on video signals, a keyboard & mouse interface (abbreviated as keyboard & mouse I/F) 45 connected to the keyboard 34b and the mouse 35b, a voice interface (abbreviated as voice I/F) 60, which captures voice signal data from the microphone 30b, a removable storage device 61, which stores image data and so on in the removable disk 61*a*, and a decrypting portion 62, which performs decrypting processing. These are connected to each other through a bus.

Control signals and so on from the second signal transmitting device 28 are communicated through the I/O 43. The operating programs for the controller 32 are stored in the HDD 41. For example, when setting for controlling an operation of the surgery tool 20 is implemented from the touch panel 25 or the like in the surgery 5 side through the first controller 24, the control content is stored in the memory 42 or the like from the I/O 43 within the controller 32 through the signal transmitting devices 27 and 28. Patient information from the I/O 43 within the controller 32 is stored in the memory 42 or the like in the same manner.

As described later, when the packet data input from the I/O 43 includes header information indicating encrypted signals, the decrypting portion 62 decrypts the encrypted patient data stored in the memory 42 to obtain patient data before the encryption.

The video capture control portion 44 is connected to the signal transmitting device 28 and includes an A/D converter 46, which A/D-converts input analog video signals and a D/A converter 47, which D/A-converts and outputs video signals.

These A/D converter 46 and D/A converter 47 are connected to the overlay control portion 48, which performs overlay-control. The overlay control portion 48 includes a video memory inside and is connected to a control circuit 49, which controls the overlay display and exchanges data. The control circuit 49 is connected to the bus.

Image communication by the signal transmitting device 28 according to this embodiment is performed through the A/D converter 46 and the D/A converter 47 included by the video capture controlling portion 44. The input analog video signals from the A/D converter 46 are image-converted in the overlay control portion 48 in accordance with the control by the control circuit 49.

The output from the overlay control portion 48 is sent to the signal transmitting device 28 through the D/A converter 47. The communication between the signal transmitting device 28 and the controller 32 is controlled by the CPU 40 in accordance with the program stored in the HDD 41.

Images captured through the video capture control portion 44 can be stored in the HDD 41. An image of the images stored in the HDD 41 may be selected by the keyboard 34. Then, the CPU 40 outputs the reduced image (thumbnail image) of the selected image to the video capture control portion 44 side. Then, the reduced image can be superimposed on the video signals (sent from the first signal transmitting device 27 side) through the overlay control portion 48.

The analog video signals from the D/A converter 47 are also output to the display device 33. For example, the display shown in FIG. 3 may be provided by the display device 33.

The controller 24 in the surgery 5 side uses an encrypting portion 65 (see FIG. 4A) instead of the decrypting portion 62 and basically includes, in addition to the construction of the controller 32 in FIG. 2, a control circuit, which controls surgery tool 20 and so on, and a super impose circuit, which outputs the combination of the patient information and video signals from the CCU 21 to the first monitor 22 instead of the video capture control portion 44.

Figure 3:
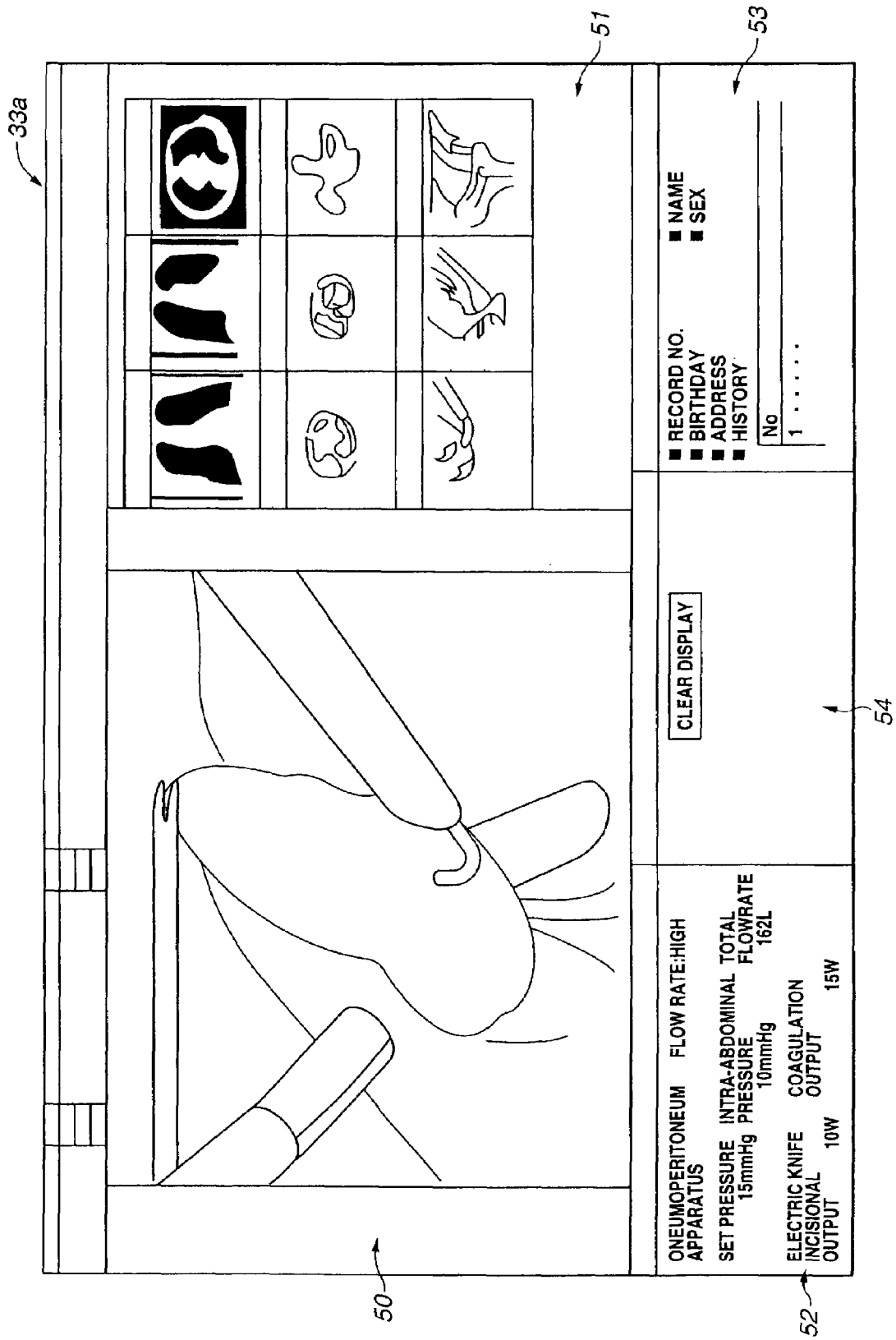

As shown in FIG. 3, a display area 33*a* of the display device 33 includes an image display area 50, a thumbnail display area 51, a surgery tool state display area 52, a patient information display area 53, and a comment display area 54.

The thumbnail display area 51 displays an image window in response to a manipulation on an image select button (not shown) displayed in a toolbar in the display area 33*a* and displays multiple images related to items corresponding to the desired and selected item (such as a patient name and a manipulation name).

The image display area 50 displays video signals from the CCU 21 included in the endoscope imaging unit and an image selected from the thumbnail display area 51.

The thumbnail display area 51 displays a reduced image and/or moving images of image data stored in the second controller 32 and a reduced still image (thumbnail image) of video signals corresponding to an endoscope image from the CCU 21.

The surgery tool state display area 52 displays states of the surgery tool body 8, the CCU 21 and so on, which are sent from the first controller 24.

The patient information display area 53 displays patient information (encrypted and) sent from the first controller 24.

A unit for sending images, voice and signals over a network may be Asynchronous Transfer Mode (ATM) or TCP/IP.

FIG. 4A shows the construction of a portion, which encrypts and transmits patient data and which decrypts the encrypted patient data.

In order to send data 71 having a packet structure, such as image data, to the controller 24, which is a sending side for sending image data and so on, through the network circuit 4, the data 71 is input to the CPU 63, which performs a control operation.

The data 71 has a packet data structure in which a header portion 72, a data portion 73 and a security bit portion 74 are aligned in time-series.

The CPU 63 determines whether or not patient information is included in the data portion 73 based on the header data of the header portion 72 in the beginning of the packet structure of the data 71. If the data portion 73 includes patient data, the CPU 63 sends it to the encrypting portion 64.

The encrypting portion 64 encrypts patient data input through the CPU 63 by using a public key 64*a* and then is sent to the signal transmitting device 27 (see FIG. 1) through an input/output interface (abbreviated as I/O) 65 for inputting/outputting (sending/receiving). Then, the signal transmitting device 27 sends it to a remote location over the network circuit 4. For simplicity, the signal transmitting device 27 is omitted in FIG. 4A.

Therefore, if the data 71 output from the I/O 65 includes patient data, a packet data structure can be obtained in which the data portion 73 in FIG. 4B is replaced by the encrypted data portion 73*a*, as shown in FIG. 4C.

On the other hand, if it is control data, the control data is input from the CPU 63 to the I/O 65 without passing through the encrypting portion 64. Therefore, the control data output from the I/O 65 is output as it is, having the packet structure shown in FIG. 4B, which is not encrypted like the image data.

The remote location side (in this case, the receiving side) inputs the signals sent through the signal transmitting device 28 to the CPU 40 through an I/O 43 included in the controller 32. The CPU 40 identifies it from the header portion 72. If it is encrypted patient data, the CPU 40 sends it to the decrypting portion 62. Then, the encrypted data is decrypted by using an encryption key (private key) 62*a* and is converted to the patient data before the encryption. Then, the patient data is displayed in the display device 33 in FIG. 1.

A second monitor 31 is connected to the signal transmitting device 28, as shown in FIG. 1. Thus, image data transmitted to the signal transmitting device 28 through the network circuit 4 can be displayed.

An operation of this embodiment having the construction will be described.

As shown in FIG. 1, the operating device portion 2 and the remote supporting device portion 3 are connected through the network circuit 4, such as ATM, and are powered on, respectively. Patient information such as a name of the patient 7 is input from the magnetic card reader 26 to the first controller 24.

The endoscope 9 is connected to the light source device 17 through the light guide cable 16 such that illustrating light can be supplied thereto. In addition, a television camera 15 is attached to the objective portion 13 of the endoscope 9. The signal cable 19 of the television camera 15 is connected to the CCU 21. An endoscope image imaged by the CCD 14 is displayed in the first monitor 22.

First of all, pneumoperitoneum apparatus is inserted to the abdominal portion of the patient 7 through a trocar, not shown. As a result, pneumoperitoneum occurs within the abdominal. Then, the inserting portion 12 of the endoscope 9 is inserted therein through the trocar such that an image of the affected part within the abdominal can be displayed in the first monitor 22.

Then, the surgery tool body 8 such as an electric knife, to be used for the operation is inserted to the abdominal of the patient 7 through the trocar.

Video signals of the endoscope images output from the CCU 21 to the first monitor 22 through the controller 24 are transmitted from the first signal transmitting device 27 to the second signal transmitting device 28 side through the circuit 4 and are displayed in the second monitor 31.

The video signals are connected so as to input to the second controller 32. Thus, the remote supporting operator can instruct from the keyboard 34 to capture a proper endoscope image showing the resected part for the operation, for example, which is displayed in the second monitor 31. The endoscope image (still image) is captured through the video capture control portion 44 of the controller 32 in response to the capture instruction from the keyboard 34. The captured endoscope image is displayed in the image display area 50, as shown in FIG. 3, of the display device 33 connected to the controller 32.

Patient information from the magnetic card reader 26, which is encrypted by the first controller 24, is input from the I/O 43 to the controller 32 through the signal transmitting devices 27 and 28. As described with reference to FIG. 4A and so on, the encrypted patient information is decrypted and is stored in the memory 42 or the like within the controller 32.

Then, the patient information is displayed at all times in the patient information display area 53 in the display device 33, as shown in FIG. 3.

Notably, voice information can be transmitted and be restructured by using a speaker, not shown, provided in the monitor 22 or 31 or the display device 33.

In this embodiment, a large amount of image information is transmitted without the encryption. On the other hand, patient information part is identified, encrypted and sent so as to protect the privacy. Therefore, only the smaller amount of patient information (identification information of the patient) than that of the image information is encrypted and sent. Thus, the transmission speed is hardly deteriorated, resulting in the fast information transmission.

In addition, according to this embodiment, the security for the privacy involving part of the medical information can be obtained at lower costs.

The sending side needs a unit for encrypting and sending patient information while the receiving side needs a unit for decrypting the encrypted patient information. However, a time for transmitting the patient information is shorter than the time for transmitting a large amount of images since the amount of the patient information is small. Therefore, slower encrypting and decrypting units can be used in practice, which results in lower costs.

For example, the CPU's 63 and 40 may also serve as the encrypting portion 64 and the decrypting portion 63 in FIG. 4A, respectively, by using software.

Figure 5:
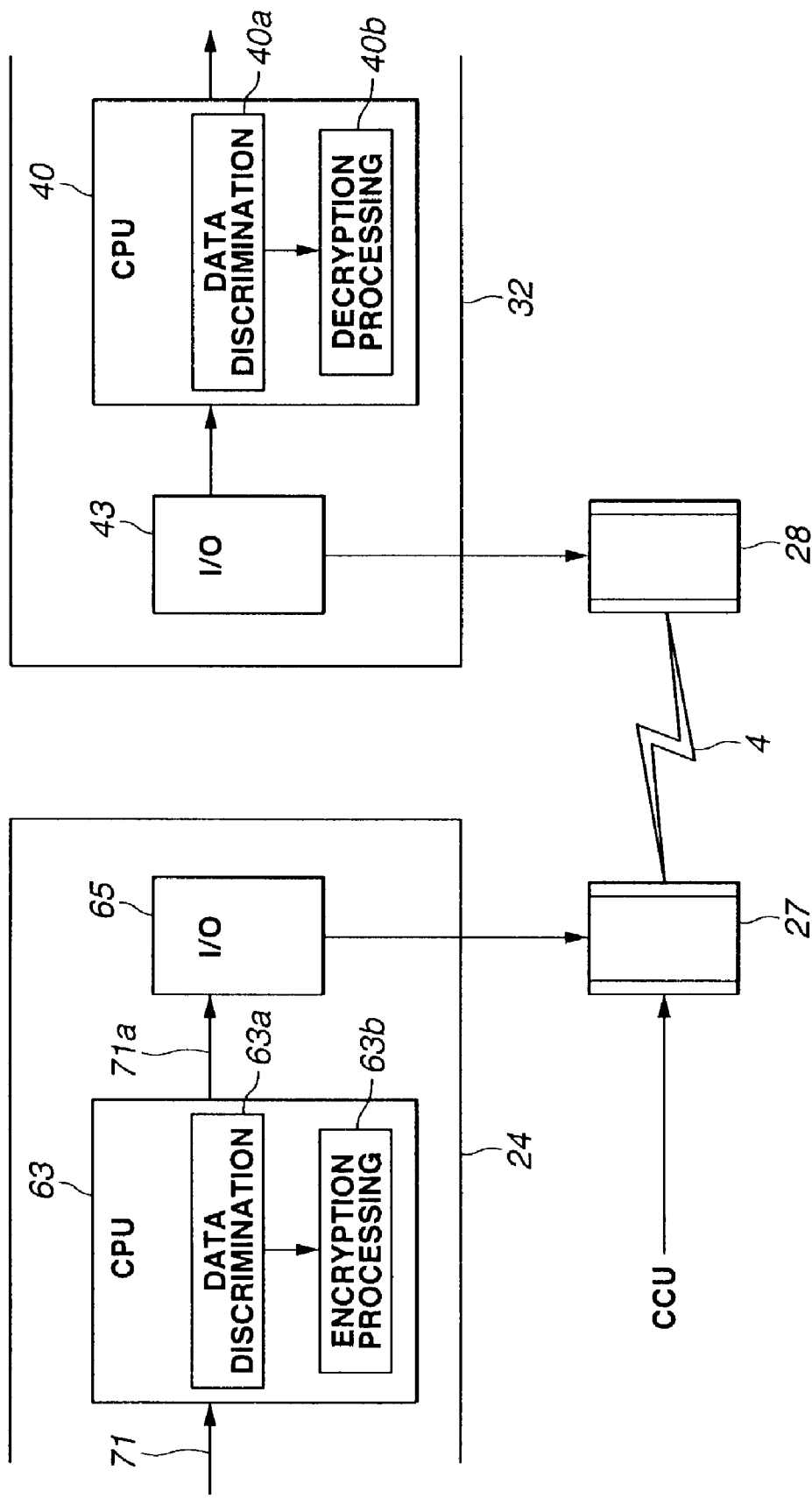

In other words, as shown in FIG. 5, when data is input to the CPU 63 within the controller 24, the CPU 63 determines whether the data is patient data (or non-patient data) from the header portion 72 of the data. That is, the CPU 63 performs data determining processing 63a.

If the data is patient data, the CPU 63 performs encrypting processing 63b on the patient data by using software and outputs it to the I/O 65. The encrypted patient data output to the I/O 65 is transmitted to the signal transmitting device 28 through the signal transmitting device 27 and the network circuit 4.

The encrypted patient data transmitted to the signal transmitting device 28 is input to the CPU 40 through the I/O 43. The CPU 40 determines whether or not the input, encrypted patient data is patient data from the header portion 72 of the patient data. That is, data determining processing 40a is performed. If the data is determined as the patient data, decrypting processing 40b is performed. Then, the encrypted patient data is decrypted and is returned to the patient data before the encryption.

In the remote supporting device portion 3 side, in order to record an image and patient data in the removable disk 61a in the removable storage device 61, such as MO, patient data before the decryption is stored therein. The patient data and the image cannot be viewed by a controller without the encryption key at the same time.

This operation is also applicable for a case where an image and patient data are recorded in a removable medium 29a by the removable storage device of the controller 24 of the operating device portion 2.

The remote supporting operator overlay-displays an endoscope image and decrypted patient information, which are sent from the surgery 5 side, in the display device 33.

The operator in the surgery 5 sets output values for resection by using, for example, an electric knife and for coagulation from the touch panel 25. Then, the control content including the output setting for the surgery tool 20 is sent from the first controller 24 to the I/O 43 of the second controller 32 and is stored in, for example, the memory 42. In addition, as shown in FIG. 3, the control information (setting information) regarding the surgery tool 20 is displayed in the surgery tool state display area 52.

In FIG. 3, the setting information regarding the pneumoperitoneum apparatus is also displayed in the surgery tool state display area 52. In other words, control information regarding multiple surgery tools can be displayed.

When the operator in the surgery 5 changes the output value of the electric knife, for example, from the touch panel 25, the changed content is sent to the I/O 43 of the second controller 32. Then, the updated content is displayed in the surgery tool state display area 52.

In other words, the control content (setting content) regarding the surgery tool 20 is displayed in the display device 33 in substantially real time. Thus, the remote supporting operator can check the state of the surgery tool 20 in substantially real time.

When the operator in the surgery 5 has a comment, the operator can input the comment from the keyboard 34*a*. Then, as shown in FIG. 3, the comment is displayed in the comment display area 54.

When the remote supporting operator responses to the comment, the response to the comment is input from the keyboard 34*b* and is sent to the surgery 5 side. The operator in the surgery 5 can realize the response by viewing, for example, the first monitor 22.

The remote supporting operator can record an endoscope image captured by the video capture control portion 44. For example, when an instruction to recording the image from the keyboard 34 is input, the still image can be recorded in the HDD 41.

The endoscope image stored in the HDD 41 can be reduced in size. Then, the reduced screen selected for the display can be displayed in the thumbnail display area 51 in FIG. 3.

In addition to the endoscope images, an X-ray image for the patient 7 can be sent from the first controller 24 to the second controller 32 in the remote supporting room 6 and be stored in the HDD 41. The reduced image of the image stored in the HDD 41 can be also displayed.

The remote supporting operator can give a proper diagnosis for the operation on the patient 7 by referring to the images in the display device 33. Thus, the remote supporting operator can provide the surgery 5 side with support information for the operation based on the diagnosis.

According to this embodiment, when image information and so on for the operation is sent to the operation supporting room, which supports the operation, over a communication circuit, whether or not the information includes patient information is determined based on the header portion of the sent data. If the information includes patient information, only the patient information part (which is a smaller amount than that of the image data) is encrypted and is sent. The larger amount of image data is sent as it is (without the encryption). Therefore, the privacy of the patient information can be protected, and the information can be sent fast without deterioration in the sending speed.

Since an amount of information to be encrypted is small, a slower measure (such as software) is only enough, which can prevent an increase in cost.

The optical endoscope 9 is not limited to the one, which transmits an optical image by using a relay lens system. The optical endoscope 9 may adopt an image guide, which transmits an optical image by using a fiber bundle.

In the above-described embodiment, an endoscope image output from the CCU 21 is displayed in the first monitor 22. A control content regarding a surgery tool and patient information are input from the controller 24 into the first monitor 22, and the control content and the patient information are superimpose-displayed on the endoscope image.

In the above-described embodiment, while the magnetic card reader 26 is adopted to input patient information, the present invention is not limited thereto. The other information recording media such as an IC card and an optical card can be used.

The surgery tool may be an ultrasonic surgery tool and the other as well as the electric knife and a pneumoperitoneum apparatus.

It is described above the case where an encrypting unit (specifically, the encrypting portion 64 in FIG. 4A) in the controller 24 side and a decrypting unit (specifically the decrypting portion 62 in FIG. 4A) are provided. However, both sides can be provided with both encrypting unit and decrypting unit.

Thus, even when the manipulation to send the patient information is performed in the remote supporting device portion 3 side, the patient information is automatically encrypted and is sent then. Therefore, the privacy can be protected.

The privacy of the patient information may be protected by using the construction of a second embodiment described below.

Figure 6:
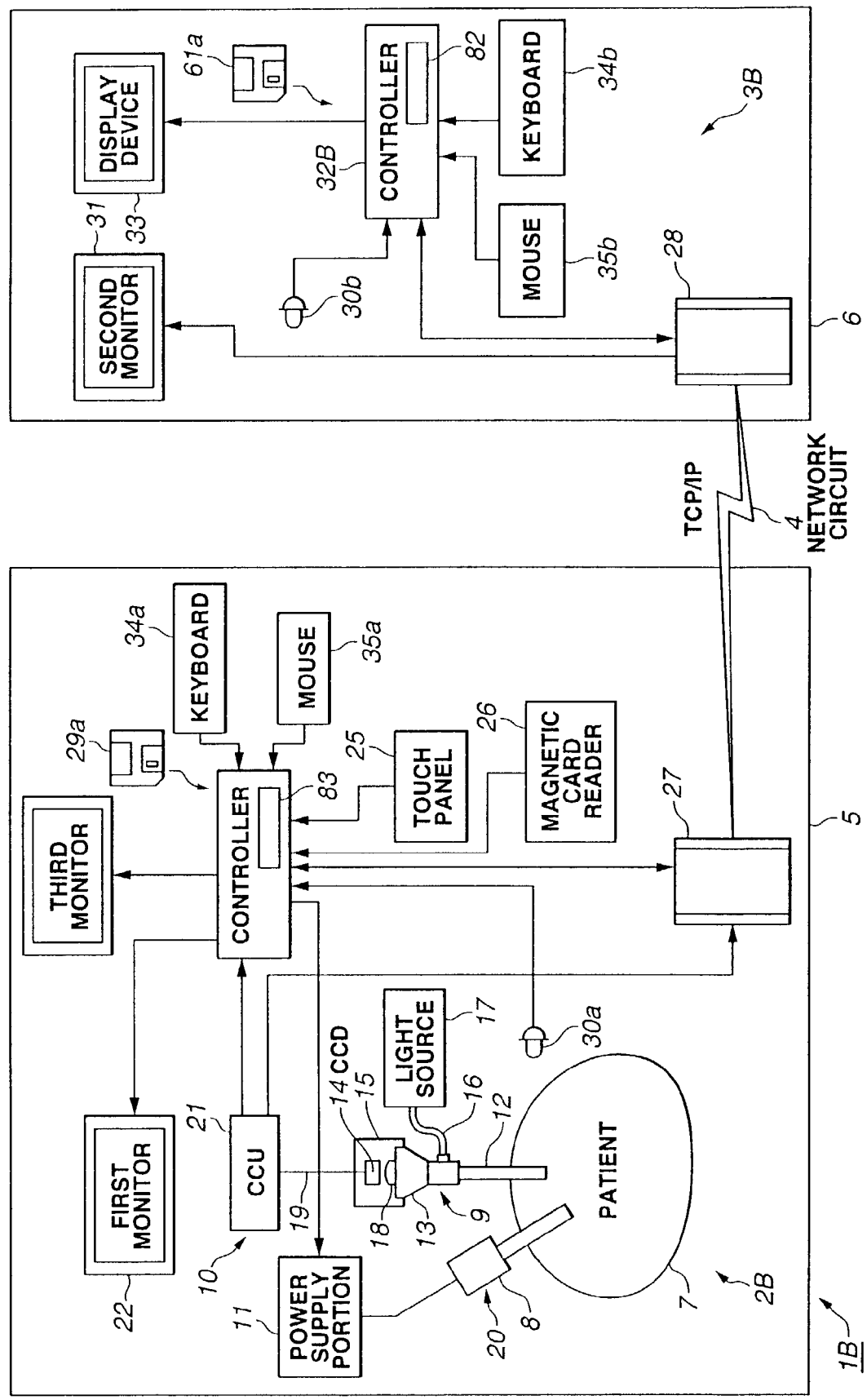
FIGS. 6 to 8 relate to a second embodiment of the present invention.

An remote medical supporting system 1B according to the second embodiment, shown in FIG. 6, has the same construction in FIG. 1 except that a controller 24B is used instead of the controller 24 in the operating device portion 2 located in the surgery 5. The operating device portion 2 is replaced by an operating device portion 2B in which the controller 24B is connected to a third monitor 81.

In addition, the remote supporting device 3 located in the remote control room 6 in FIG. 1 is replaced by a remote supporting device portion 3B, which adopts a controller 32B instead of the controller 32.

The third monitor 81 displays image information and so on sent from the remote control room 6 side.

The controller 32B has the same construction as that of the controller 32 in FIG. 2 except that an encrypting portion 82 is provided in addition to a decrypting portion 62. Here, the data encrypted based on the data in the header portion in received information is decrypted. In order to send information, data such as patient data is encrypted in the encrypting portion 82.

The controller 24B in the operating device portion 2B basically performs the same operations as those performed by the controller 24 according to the first embodiment except that data encrypted based on the data in the header portion of information sent from the remote control room 6 side is decrypted in the decrypting portion 83. Image information and so on, which are not encrypted, is not decrypted and are output to the third monitor 81.

Figure 7:
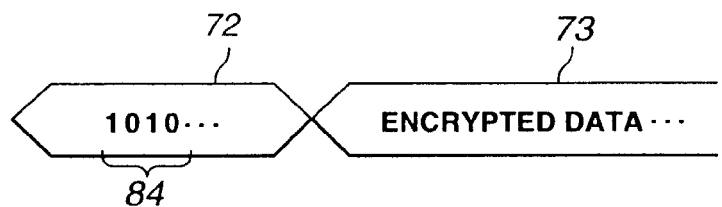

According to this embodiment, when patient data is encrypted, an identifier code 84 indicating that the patient data is encrypted is added to the header portion 72 as shown in FIG. 7. It can be easily determined, from the presence of the identifier code 84, whether or not the decryption is necessary.

Figure 8:
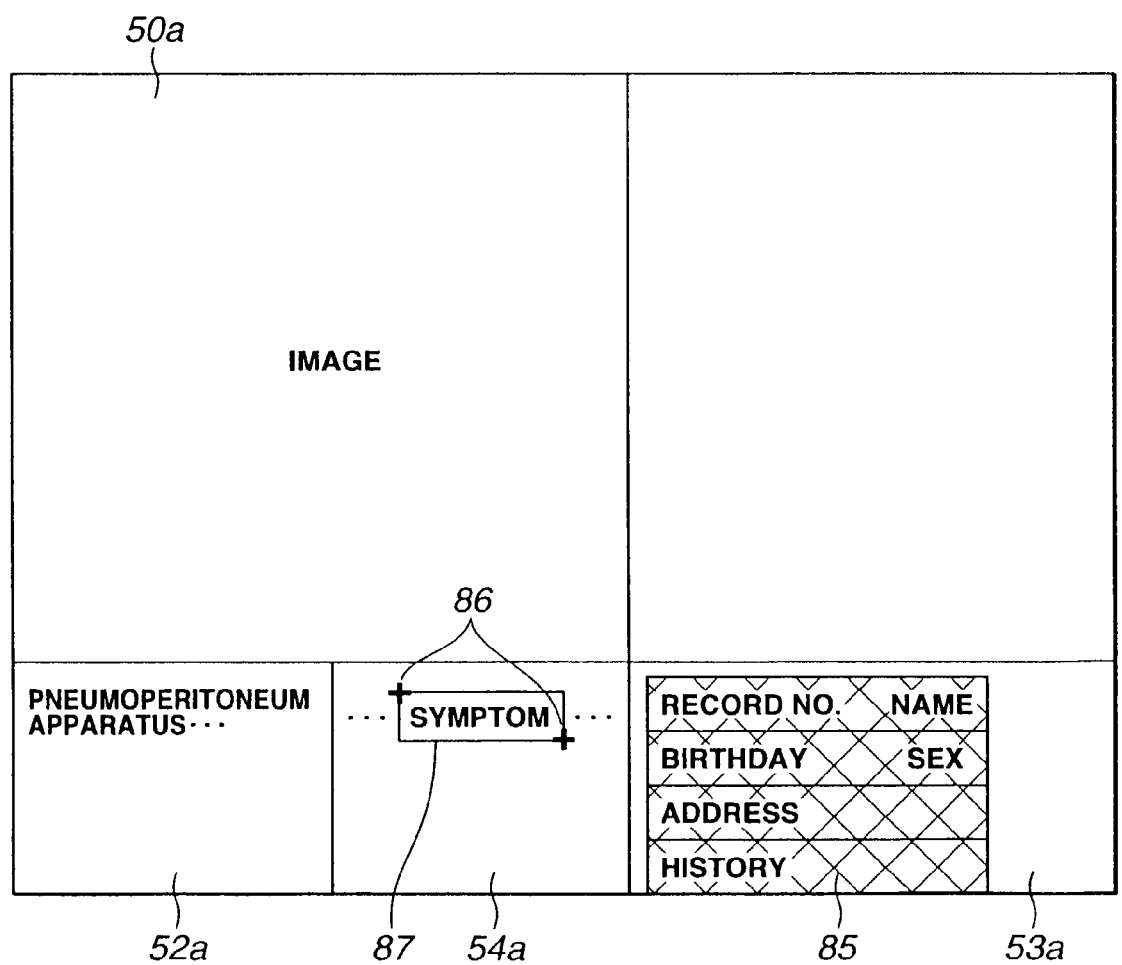

As shown in FIG. 8, in the first monitor 22, an endoscope image is displayed in an image display area 50*a*. A surgery tool state display area 52*a*, a patient information display area 53*a*, and a comment display area 54*a* are located around the image display area 50*a*. Patient data including character information such as a record number (which is identification information of the patient), the patient's name, birthday, sex, address and history, which are patient information, in the patient information display area 53*a* is encrypted and is sent.

In this case, according to this embodiment, the display using a shade 85 or a different display color may be adopted in order to easily distinguish between the data part to be encrypted and be sent as such and the data part including character information, which is not encrypted like the data part in the surgery tool state display area 52*a*.

When a comment is written in the comment display area 54*a* and the comment is sent, a confirmation display asking if the comment is okay to sent or not before the transmission is displayed in the comment display area 54a. If OK is input, the comment may be sent actually.

In this case, when a part of the comment, for example, includes information relating to a symptom of the patient, the part or the entire comment may be specified for the encryption into an area 87 by using a cursor 86. Then, the character information within the area 87 can be encrypted. In this case, when the character information in the area 87 is sent, the identifier code 84 shown in FIG. 7 is given to the header portion. In the receiving side, the presence of the identifier code 84 is identified and is decrypted if any.

Accordingly, the leak of information relating to patient's symptom, for example, can be prevented.

Before determining whether or not the decryption is performed by the decrypting unit, a manipulation to input an ID of a user may be required only when a specific ID is input, the decrypting unit may be performed.

Thus, the leak of patient information can be prevented when a person who does not relate to the operation performs some manipulation.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An operation supporting system, which support an operation by sending information on the operation, comprising:
   an operating device including
      an imaging device for imaging a subject part of a patient and for outputting a real-time image signal;
      an information input device for inputting identification information of the patient and an identifier for indicating whether the identification information of the patient is encrypted or not;
      a first controller for encrypting or not encrypting the identification information of the patient input from the information input device according to the identifier without encrypting the real-time image signal; and
      a sending device for sending an encrypted or not encrypted information of the patient according to the identifier, and the identifier and the real time image signal output from the imaging device;
   a remote support device, said remote support device is located in a room remote from said operating device, said remote support device including
      a receiving device for receiving the encrypted information of the patient, the identifier and the real-time image signal sent from the sending device;
      a second controller for decrypting the information of the patient received by the receiving device only when the identifier indicates that the information of the patient is encrypted; and
      a display device for displaying the identification information of the patient via the second controller and the real-time image signal from the receiving device.

2. An operation supporting system according to claim 1, wherein the imaging device comprises an endoscope including an imaging element.

3. An operation supporting system according to claim 2, wherein the imaging device comprises a signal processing device for performing signal processing on the imaging element and for outputting the real-time image signal.

4. An operation supporting system according to claim 1, wherein the information input device comprises at least one of a magnetic card reader, an optical card reader, a keyboard and an IC card reader.

5. An operation supporting system according to claim 1, wherein the first controller uses a public key when the identification information is encrypted.

6. An operation supporting system according to claim 1, wherein the second controller uses a private key when the encrypted information is decrypted.

7. An operation supporting system according to claim 1, wherein processing for encrypting the identification information is performed by a CPU.

8. An operation supporting system according to claim 1, wherein processing for decrypting the encrypted information is performed by a CPU.

9. An operation supporting system according to claim 1, wherein the sending device can also send voice information.

10. An operation supporting system according to claim 1, wherein an image signal from the imaging device is input to the sending device without passing through the first controller.

11. An operation supporting system according to claim 1, wherein an analog image signal is input from the imaging device to the sending device.

12. An operation supporting system according to claim 1, wherein the sending device and the receiving device are connected through a communication circuit.

13. An operation supporting system according to claim 1, wherein the encrypted information includes information in which patient information relating to the patient is encrypted in addition to information in which identification information of the patient is encrypted.

14. An operation supporting system according to claim 1, wherein the first controller encrypts patient information relating to a specific patient in addition to the identification information.

15. An operation supporting system according to claim 1, wherein the receiving device has a sending function for sending real-time information, and the sending device has a receiving function for receiving real-time information sent by the sending function of the receiving device.

16. An operation supporting system according to claim 15, wherein the receiving device encrypts and sends information when the real-time information is identification information of a specific patient.

17. An operation supporting system according to claim 1, further comprising a second display device, located in close proximity to said operating device, for displaying an image signal from the imaging device and the identification information input from the information input device.

18. An operation supporting system according to claim 17, wherein the encrypted information is provided, in the header portion, with an identification code indicating that the information is encrypted.

19. An operation supporting system according to claim 17, wherein an encrypted information part in display information can be displayed in the second display device such that the part can be distinguished from character information, which is not encrypted.

20. An operation supporting system according to claim 1, wherein character information to be encrypted and to be sent can be specified.

21. The operation support system according to claim 1, wherein the identifier is added to a header portion of the identification information of the patient.

22. The operation support system according to claim 1, wherein the identifier is an identifier code for indicating by code whether the identification information of the patient sent from the sending device is encrypted or not encrypted.

23. An operation supporting apparatus for sending information on an operation, comprising:
- an imaging device for imaging a subject part of a patient and for outputting a real-time image signal;
- an information input device for inputting identification information of the patient and an identifier for indicating whether the identification information of the patient is encrypted or not;
- a controller for encrypting or not encrypting the identification information of the patient input from the information input device according to the identifier without encrypting the real-time image signal; and
- a sending device located in close proximity of the patient for sending an encrypted or not encrypted information of the patient according to the identifier, the identifier and the real-time image signal output from the imaging device.

24. An operation supporting apparatus according to claim 23, further comprising:
- a remote support device, said remote support device is located in a room remote from said operating device, said remote support device including:
  - a receiving device for receiving the information of the patient, the identifier and the real-time image signal sent from the sending device;
  - a second controller for decrypting the information of the patient received by the receiving device only when the identifier indicates that the information of the patient is encrypted; and
  - a display device for displaying the identification information of the patient the second controller and the real-time image signal from the receiving device.

* * * * *

UNITED STATES PATENT AND TRADEMARK OFFICE
CERTIFICATE OF CORRECTION

PATENT NO. : 7,386,730 B2  
APPLICATION NO. : 10/234875  
DATED : June 10, 2008  
INVENTOR(S) : Akinobu Uchikubo Page 1 of 1

It is certified that error appears in the above-identified patent and that said Letters Patent is hereby corrected as shown below:

<u>Column 14, Claim 24, Line 16:</u>

"information of the patient the second controller and the"

should read

--information of the patient via the second controller and the--

Signed and Sealed this

Second Day of September, 2008

JON W. DUDAS  
*Director of the United States Patent and Trademark Office*